US009855222B2

(12) United States Patent
Redmond et al.

(10) Patent No.: US 9,855,222 B2
(45) Date of Patent: Jan. 2, 2018

(54) TOPICAL SANITIZER THAT INCLUDES AVENANTHRAMIDES

(71) Applicant: The Idea Folder LLC, Green Bay, WI (US)

(72) Inventors: Mark James Redmond, Edmonton (CA); Joseph H. Neuser, Green Bay, WI (US)

(73) Assignee: The Idea Folder LLC, Green Bay, WI (US)

( * ) Notice: Subject to any disclaimer, the term of this patent is extended or adjusted under 35 U.S.C. 154(b) by 6 days.

(21) Appl. No.: 14/672,057

(22) Filed: Mar. 27, 2015

(65) Prior Publication Data
US 2016/0279075 A1  Sep. 29, 2016

(51) Int. Cl.
| | | |
|---|---|---|
| A61K 31/045 | (2006.01) | |
| A61K 8/42 | (2006.01) | |
| A61Q 17/00 | (2006.01) | |
| A61Q 19/10 | (2006.01) | |
| A01N 31/02 | (2006.01) | |
| A01N 37/24 | (2006.01) | |
| A01N 25/04 | (2006.01) | |
| A01N 65/44 | (2009.01) | |

(52) U.S. Cl.
CPC ............ *A61K 31/045* (2013.01); *A01N 25/04* (2013.01); *A01N 31/02* (2013.01); *A01N 37/24* (2013.01); *A01N 65/44* (2013.01); *A61K 8/42* (2013.01); *A61Q 17/005* (2013.01); *A61Q 19/10* (2013.01)

(58) Field of Classification Search
CPC ........ A01N 31/02; A61K 31/045; A61K 8/42; A61Q 17/005; A61Q 19/10
See application file for complete search history.

(56) References Cited

U.S. PATENT DOCUMENTS

| | | | |
|---|---|---|---|
| 3,059,241 A | 10/1962 | O'Brien et al. | |
| 3,942,193 A | 3/1976 | Pugh | |
| 4,853,978 A | 8/1989 | Stockum | |
| 5,014,362 A | 5/1991 | Tillotson et al. | |
| 5,133,090 A | 7/1992 | Modak et al. | |
| 5,219,340 A | 6/1993 | Seneca | |
| 5,534,350 A | 7/1996 | Liou | |
| 5,641,494 A | 6/1997 | Cauwenbergh | |
| 5,691,287 A | 11/1997 | Villars et al. | |
| 5,830,884 A | 11/1998 | Kasica et al. | |
| 6,000,061 A | 12/1999 | Taneja et al. | |
| 6,004,584 A | 12/1999 | Peterson et al. | |
| 6,416,788 B1 | 7/2002 | Barr | |
| 6,818,232 B1 | 11/2004 | Redmond et al. | |
| 6,953,582 B2 | 10/2005 | Chou | |
| 7,691,436 B2 | 4/2010 | Neuser et al. | |
| 7,718,240 B2 | 5/2010 | Neuser et al. | |
| 7,740,622 B2 | 6/2010 | Neuser et al. | |
| 8,075,965 B2 | 12/2011 | Neuser et al. | |
| 8,431,142 B2 | 4/2013 | Redmond et al. | |
| 8,871,233 B2 | 10/2014 | Redmond et al. | |
| 2002/0017493 A1 | 2/2002 | Ehrnsperger et al. | |
| 2005/0037054 A1 | 2/2005 | Hamann | |
| 2005/0076917 A1 | 4/2005 | Wray et al. | |
| 2005/0081278 A1 | 4/2005 | Williams | |
| 2007/0059390 A1 | 3/2007 | Magee et al. | |
| 2007/0184186 A1 | 8/2007 | Neuser et al. | |
| 2008/0003273 A1 | 1/2008 | Feldkamp et al. | |
| 2008/0234160 A1 | 9/2008 | Wenzel et al. | |
| 2008/0268077 A1 | 10/2008 | Vielhaber | |
| 2009/0191248 A1 | 7/2009 | Hoffman et al. | |
| 2010/0229281 A1 | 9/2010 | Neuser et al. | |
| 2012/0102620 A1 | 5/2012 | Neuser et al. | |
| 2012/0171280 A1 | 7/2012 | Zhang | |
| 2012/0214878 A1 | 8/2012 | Korb et al. | |
| 2012/0294911 A1* | 11/2012 | Redmond ............ | A61K 36/899 424/401 |
| 2013/0224273 A1 | 8/2013 | Redmond et al. | |
| 2015/0258003 A1* | 9/2015 | Copeland ............... | C11D 7/261 424/78.07 |

OTHER PUBLICATIONS

Becker, "Use of Colloidal Oatmeal Inside Rubber Gloves", AMA Archives of Dermatology, 1955:71( ), p. 378 (1955).
Sompayrac et al., "Colloidal Oatmeal in Atopic Dermatitis of the Young", Journal of the Florida Medical Association, vol. 45 No. 12 p. 1411-1412, (Jun. 1959).
White et al., "Colloidal Oatmeal as Dusting Powder for Surgical Gloves", Modern Hospital, vol. 93, No. 4, p. 129-130 (Oct. 1959).
Feigenbaum, "Colloidal Oatmeal for Skin Eruptions", Journal of the Medical Society of New Jersey, vol. 54, No. 7, p. 330-331 (Jul. 1957).
Grais, "Role of Colloidal Oatmeal in Dermatologic Treatment of the Aged", A.M.A. Archives of Dermatology and Syphilology, vol. 68 No. 4 p. 402-407 (Oct. 1953).
Yiu et al, Abstract, "Effect of Cooking on Starch and Beta-Glucan of Rolled Oats", Cereal Chem. 64, p. 373-379 (1987).
Hamann, "Review of Natural Rubber Latex Protein Allergy", American Journal of Contact Dermatitis, vol. 4 No. 1, p. 1 and 5 (1993).
"The Only Glove Powdered with Oats", Ostar glove brochure (1997).

(Continued)

*Primary Examiner* — Michael B. Pallay
(74) *Attorney, Agent, or Firm* — Martin & Associates, LLC; Derek P. Martin

(57) ABSTRACT

Topical sanitizers including alcohol-based gels, alcohol-based foams, alcohol-free foams, liquid soaps, alcohol-based wipes, and alcohol-based sprays include avenanthramides, which is an active component of oats that is beneficial to the skin. The concentration of avenanthramides can be substantially less when considering the use profile of the person using the sanitizers. Many healthcare workers sanitize their hands dozens of times a day. An effective dose of avenanthramides can be delivered to the skin even when the concentration in avenanthramides is relatively low due to the repeated application of the sanitizers during the day. In addition, a lower concentration of avenanthramides may be used to maintain healthy skin compared to a higher concentration that may be used to repair damaged skin. Minimum concentrations of avenanthramides in one or more topical sanitizers can be determined according to the use profile and the target amount of avenanthramides to deliver via the topical sanitizers.

11 Claims, 8 Drawing Sheets

(56) References Cited

OTHER PUBLICATIONS

Swanson et al, "Latex Allergen Affinity for Starch Powders Applied to Natural Rubber Gloves and Released as an Aerosol: From Dust to Don", Canadian Journal of Allergy and Clinical Immunology, vol. 5 No. 8, p. 330-336 (2000).

Henry Schein Dental '97 Catalog, p. 158 showing advertisement for Ultravena Ostar latex exam gloves that contain Oat Starch (1997).

Ultravena, "The Natural Solution to Skin Irritation for the Health Care Professional" (1994).

Foreign patent abstract from publication RD 505011A, May 10, 2006.

Safeguard(R) AntiBacterial Foaming Hand Soap product label, Jul. 1, 2010, accessed online at http://www.drugs.com/otc/1 04111 /safeguard-antibacterial-foaming.html on Dec. 9, 2013.

\* cited by examiner

| Target Amount | Purpose |
|---|---|
| 0.1 microgram/day | Skin Maintenance |
| 1.0 microgram/day | Skin Repair/Relief |

FIG. 10

| Dentist – 56 applications/day | | |
|---|---|---|
| Target Amount | Purpose | Minimum Concentration |
| 0.1 microgram/day | Skin Maintenance | 0.0018 microgram per 1.8 ml application = 0.001 ppm |
| 1.0 microgram/day | Skin Repair/Relief | 0.018 microgram per 1.8 ml application = 0.01 ppm |

FIG. 11

| Nurse – 96 applications/day | | |
|---|---|---|
| Target Amount | Purpose | Minimum Concentration |
| 0.1 microgram/day | Skin Maintenance | 0.00104 microgram per 1.8 ml application = 0.00058 ppm |
| 1.0 microgram/day | Skin Repair/Relief | 0.0104 microgram per 1.8 ml application = 0.0058 ppm |

FIG. 12

| Nurse |||
|---|---|---|
| Target Amount | Purpose | Minimum Concentration |
| 0.1 microgram/day | Skin Maintenance | Alcohol-based Sanitizer<br>0.001 ppm X 1.8 ml/application X 40 applications/day = 0.072 micrograms/day |
| ^ | ^ | Soap<br>Need 0.1 – 0.072 = 0.028 micrograms/day / (56 applications/day X 1.8 ml/application) = 0.00028 ppm |
| 1.0 microgram/day | Skin Repair/Relief | Alcohol-based Sanitizer<br>0.001 ppm X 1.8 ml/application X 40 applications/day = 0.072 micrograms/day |
| ^ | ^ | Soap<br>Need 1.0 – 0.072 = 0.928 micrograms/day / (56 applications/day X 1.8 ml/application) = 0.00921 ppm |

FIG. 13

TOPICAL SANITIZER THAT INCLUDES AVENANTHRAMIDES

BACKGROUND

1. Technical Field

This disclosure generally relates to topical sanitizers, and more specifically relates to topical sanitizers that include skin-conditioning ingredients such as avenanthramides.

2. Background Art

There are many jobs today that require a person to have sanitized hands, such as foodservice and healthcare. There are many known sanitizers a person can use to sanitize the hands, including various soaps, alcohol-based sanitizers, alcohol-free sanitizing foams, etc. The goal of a sanitizer is to sanitize a person's hands by killing germs, thereby providing hands that cannot transmit germs to things that come in contact with the person's hands, such as people, food, surfaces, etc.

There are also many public locations that offer hand sanitizer for people to use, including clinics, hospitals, gymnasiums, banks, schools, movie theaters, restaurants, public restrooms, etc. Hand sanitizers have become very popular in a variety of different settings. Some hand sanitizers have a tendency to dry out the skin by removing the oil on the skin. While an occasional use of a hand sanitizer may not have a detrimental effect on the skin, repeated, frequent usage can lead to skin irritation and damage.

Many people in various occupations, such as foodservice and healthcare, must wear protective gloves. A problem encountered by many people who wear protective gloves for most of the workday is skin irritation. The gloves trap perspiration on the skin and do not allow air flow that would normally help to evaporate the perspiration, thereby subjecting a person's hands to a damp or wet environment for most of the day. This can lead to skin irritation. The types of skin irritation caused by protective gloves have been well-documented over the years.

Healthcare workers typically sanitize their hands both before donning gloves and after removing gloves. Alcohol-based gels and liquid soaps are the most commonly-used topical sanitizers. Repeated and frequent usage of some sanitizers has a tendency to cause skin sensitization, irritation, damage, dermatitis or eczema.

BRIEF SUMMARY

Topical sanitizers including alcohol-based gels, alcohol-based foams, alcohol-free foams, liquid soaps, alcohol-based wipes, and alcohol-based sprays include avenanthramides, which is an active component of oats that is beneficial to the skin. The concentration of avenanthramides can be substantially less when considering the use profile of the person using the sanitizers. Many healthcare workers sanitize their hands dozens of times a day. An effective dose of avenanthramides can be delivered to the skin even when the concentration in avenanthramides is relatively low due to the repeated application of the sanitizers during the day. In addition, a lower concentration of avenanthramides may be used to maintain healthy skin compared to a higher concentration that may be used to repair damaged skin. Minimum concentrations of avenanthramides in one or more topical sanitizers can be determined according to the use profile and the target amount of avenanthramides to deliver via the topical sanitizers.

The foregoing and other features and advantages will be apparent from the following more particular description, as illustrated in the accompanying drawings.

BRIEF DESCRIPTION OF THE SEVERAL VIEWS OF THE DRAWING(S)

The disclosure will be described in conjunction with the appended drawings, where like designations denote like elements, and:

FIG. 10 is a chart showing possible target amounts of avenanthramides for two different purposes;

FIG. 11 is a chart showing minimum concentration of avenanthramides for the dentist with the use profile in FIG. 6 according to the target amount of avenanthramides and the use profile;

FIG. 12 is a chart showing minimum concentration of avenanthramides for the nurse with the use profile in FIG. 8 according to the target amount of avenanthramides and the use profile; and FIG. 13 is a chart showing how minimum concentrations of avenanthramides can be determined in two different topical sanitizers according to the target amount of avenanthramides and the use profile.

DETAILED DESCRIPTION

Figure 1:
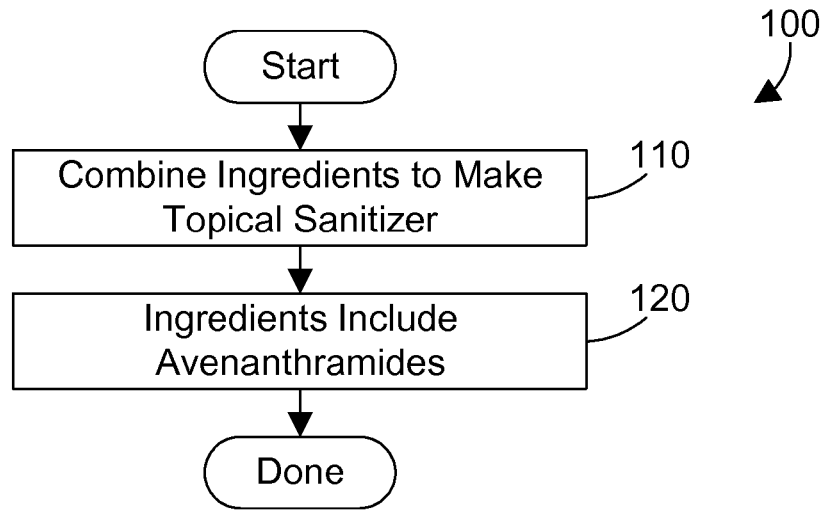
FIG. 1 is a flow diagram of a method for making a topical sanitizer that includes avenanthramides.

As stated in the Background Art section above, wearing gloves all day long can be hard on the skin of a person's hands. The gloves trap moisture on the skin and inhibit air flow that prevents the normal evaporation of the moisture on the skin. As a result, many people who use gloves extensively develop various forms of contact dermatitis, or skin irritation, that is caused by the gloves. Needless to say, subjecting already irritated skin to repeated irritations every day can create greater irritation. Sites of irritation may lead to a breakdown of the protective barrier role of the skin leaving the person vulnerable to infection. With many people whose jobs require they wear gloves, they are left with few options for preventing or treating skin problems that result from wearing the gloves.

Many people such as healthcare professionals must put on and take off gloves dozens of times each day, cleansing their hands before and after they take off gloves. Many soaps include harsh detergents that remove most of the natural oils in the outer layers of skin. Thus, repeated washings throughout the workday can dry out and irritate the skin. Alcohol-based gels can have a similar drying effect on the skin. The dryness can cause skin irritation.

One way to potentially improve the problem of skin irritation due to wearing gloves is to use topical sanitizers that include avenanthramides before putting on gloves and after taking off gloves. These sanitizers can include alcohol-based gels, alcohol-based foams, alcohol-free foams, liquid soaps, alcohol-based wipes, alcohol-based sprays, etc. Including avenanthramides in a hand sanitizer provides beneficial effects because the sanitizer works on the surface of the skin to kill the germs while the avenanthramides penetrate the skin and provide continued benefit to the skin even after the sanitizer is no longer on the surface of the skin. The penetrating action of the avenanthramides is enhanced the more a person rubs the sanitizer on the skin. The avenanthramides in the sanitizers are skin conditioners that help to keep healthy skin healthy, and can help to repair damaged skin.

The problem of skin irritation created by extensive hand washing is alleviated by the disclosure and claims herein. A topical sanitizer contains avenanthramides, which are a component of oats that has great benefits for the skin. As used herein, the term "sanitizer" refers to a substance that cleanses the skin and kills germs. Recent research has shown that avenanthramides are the components in oats that provide anti-irritant properties to skin. Avenanthramides may be extracted from oats using any suitable process, including the process disclosed in U.S. Pat. No. 6,818,232 issued on Nov. 16, 2004 to Redmond et al. The topical sanitizer may be a liquid soap, including a foam soap, so a person who is used to washing his or her hands before donning gloves and after removing gloves can continue the normal routine by substituting the liquid soap that contains avenanthramides for the normal soap. In the alternative, the topical sanitizer may be an alcohol-based gel, an alcohol-based foam, an alcohol-free foam, alcohol-based wipes, alcohol-based sprays, etc. These allow a person to cleanse and sanitize his or her hands before donning gloves and after removing gloves without washing with water. Some of the topical sanitizers disclosed herein contain relatively low levels of surfactants to avoid drying out the skin, in addition to avenanthramides to treat the skin, and may also optionally include zinc as a skin protectant. When a person sanitizes his or her hands with the topical sanitizers disclosed herein, the result is the depositing of avenanthramides, which provides great benefit to the skin. The result is a significant decrease in skin irritation on a person's hands that would normally occur from extensive wearing of gloves and sanitizing hands.

Referring to FIG. 1, a method 100 combines ingredients to make a topical sanitizer (step 110). These ingredients include avenanthramides (step 120). Note the term "topical sanitizer" means any substance that includes avenanthramides that may be used to sanitize a person's hands, including without limitations gels, foams, soaps, etc. The disclosure herein expressly details three specific embodiments of topical sanitizer, namely alcohol-based gel, foam soap, and alcohol-free foam, but the disclosure and claims are not limited to these specific embodiments.

Figure 2:
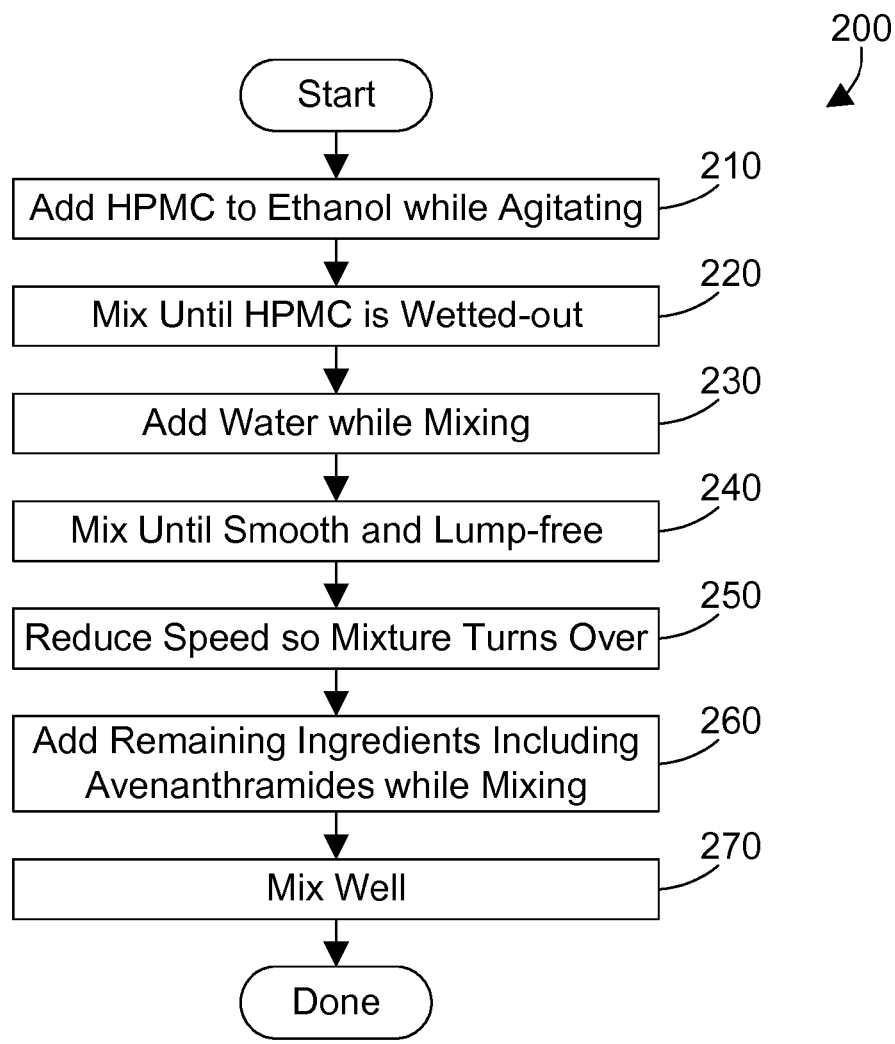
FIG. 2 is a flow diagram of a method for manufacturing an alcohol-based topical sanitizer that includes avenanthramides.

Referring to FIG. 2, a method 200 for making an alcohol-based topical sanitizer starts by adding Hydroxypropyl Methylcellulose (HPMC) to ethanol while agitating to make a slurry (step 210). The mixture is mixed until the HPMC is wetted-out (step 220). Mixing for 10 minutes is normally sufficient to wet-out the HPMC. Water is then added to the slurry while mixing (step 230). The resulting mixture is then mixed until the mixture is smooth and lump-free (step 240). Mixing for 45 minutes is typically sufficient. The mixing speed is then reduced so the mixture "turns over" (step 250). Other ingredients including avenanthramides are added while mixing (step 260). The mixture is then mixed well (step 270). Mixing for 10 more minutes is typically sufficient. Because the ethanol can easily evaporate in an open system, the preferred mixing system used in method 200 is a closed system.

One form of avenanthramides that is commercially available is a product known as colloidal oat extract distributed by Ceapro Inc., Suite 4174 Enterprise Square, 10320 Jasper Avenue, Edmonton, Alberta, Canada T5J 4P6. The colloidal oat extract is formulated to 100 parts per million (ppm) avenanthramides in a glycerin:water 1:1 base. For example, the colloidal oat extract could be made by preparing a solution of 10 mg avenanthramides in 50 grams of water and 50 grams of glycerin. Because the colloidal oat extract includes glycerin and water, the amount of colloidal oat extract to use in the formulations below can be determined mathematically from the avenanthramides concentration, which will result in a corresponding reduction in the amount of glycerin needed.

The specific ingredients and proportions for the alcohol-based sanitizing gel are preferably:

| | |
|---|---|
| Ethanol (Absolute Ethyl alcohol) | >62 grams |
| Glycerin | >0.1 grams |
| Vitamin E USP (DL-alpha tocopheryl acetate) | >0.1 grams |
| Hydroxy Propyl Methyl Cellulose (HPMC) | >1 grams |
| Avenanthramides | determined by use profile |
| Deionized water | balance to make 100 gram batch |

A suitable combination of these ranges will preferably sum to 100 grams, which means the numbers also express a percentage of each ingredient by weight in the gel. The alcohol-based sanitizing gel may also include zinc acetate. Zinc acetate is a proven skin protectant, and has received a USP monograph as a skin protectant. For the specific formulation above, a range of 0.1 to 2.0 grams of zinc acetate could be added to the mixture to enhance the skin-protecting properties of the alcohol-based sanitizer gel.

The specific ingredients and proportions for the alcohol-based sanitizing gel are more preferably:

| | |
|---|---|
| Ethanol (Absolute Ethyl alcohol) | 0.62-80 grams |
| Glycerin | 1.0-2.0 grams |
| Vitamin E USP (DL-alpha tocopheryl acetate) | 0.2-1.0 grams |
| Hydroxy Propyl Methyl Cellulose (HPMC) | 1.0-1.75 grams |
| Avenanthramides | determined by use profile |
| Deionized water | balance to make 100 gram batch |

Zinc acetate could also be added to this formulation. A range of 0.1 to 0.5 grams of zinc acetate could be added to the mixture to enhance the skin-protecting properties of the alcohol-based sanitizer gel.

The specific ingredients and proportions for the alcohol-based sanitizing gel are most preferably:

| | |
|---|---|
| Ethanol (Absolute Ethyl alcohol) | 65.00 grams |
| Glycerin | 1.50 grams |
| Vitamin E USP (DL-alpha tocopheryl acetate) | 0.5 grams |
| Hydroxy Propyl Methyl Cellulose (HPMC) | 1.50 grams |
| Avenanthramides | determined by use profile |
| Deionized water | balance to make 100 gram batch |

Note these ingredients sum to 100 grams, which means the numbers also express a percentage of each ingredient by weight in the gel. Zinc acetate could also be added to this formulation. The most preferred proportion of zinc acetate is 0.2 percent by weight of the alcohol-based sanitizer gel. Note the addition of zinc acetate will require a corresponding reduction in one of the other ingredients to keep the total weight of the formulation at 100 grams, so the numbers still reflect percent by weight of the total. In this most preferred implementation, the amount of deionized water is reduced to account for the addition of the zinc acetate. Because zinc is a skin protectant, adding zinc acetate to the alcohol-based sanitizer gel allows the alcohol-based sanitizer gel to claim skin protectant properties.

While the specific ingredients in the example above include HPMC, this is only one possible thickening agent that could be used within the scope of the disclosure and claims herein. Other suitable thickening agents could include gelling agents, for example, cellulose derivatives; carbomer gels, for example polyacrylic acid (PAA); gums, for example, tragacanth and xanthan gum; gelatin; and alum salts, for example, magnesium aluminum silicate. For alcohol-based gels, a thickening agent will typically be used so the sanitizer is a gel instead of a liquid. For alcohol-based wipes or sprays, no thickening agent is needed.

While the alcohol listed in the specific proportions above is ethanol, other alcohols or combinations of alcohols could be used. For the alcohol-based sanitizing gels disclosed herein, the alcohol is preferably selected from the group: ethanol, isopropanol and n-propanol. Of course, other alcohols or combinations of alcohols could also be used.

The specific ingredients and proportions above can be generalized. For example, the alcohol-based sanitizing gel could include any formulation that includes alcohol, a thickening agent, a concentration of avenanthramides, and may include other optional skin conditioning agents, such as glycerin, vitamin E or other emollients. To generalize even further, the disclosure and claims herein expressly extend to any topical sanitizer that includes any alcohol and a concentration of avenanthramides less than 0.01 ppm.

Figure 3:
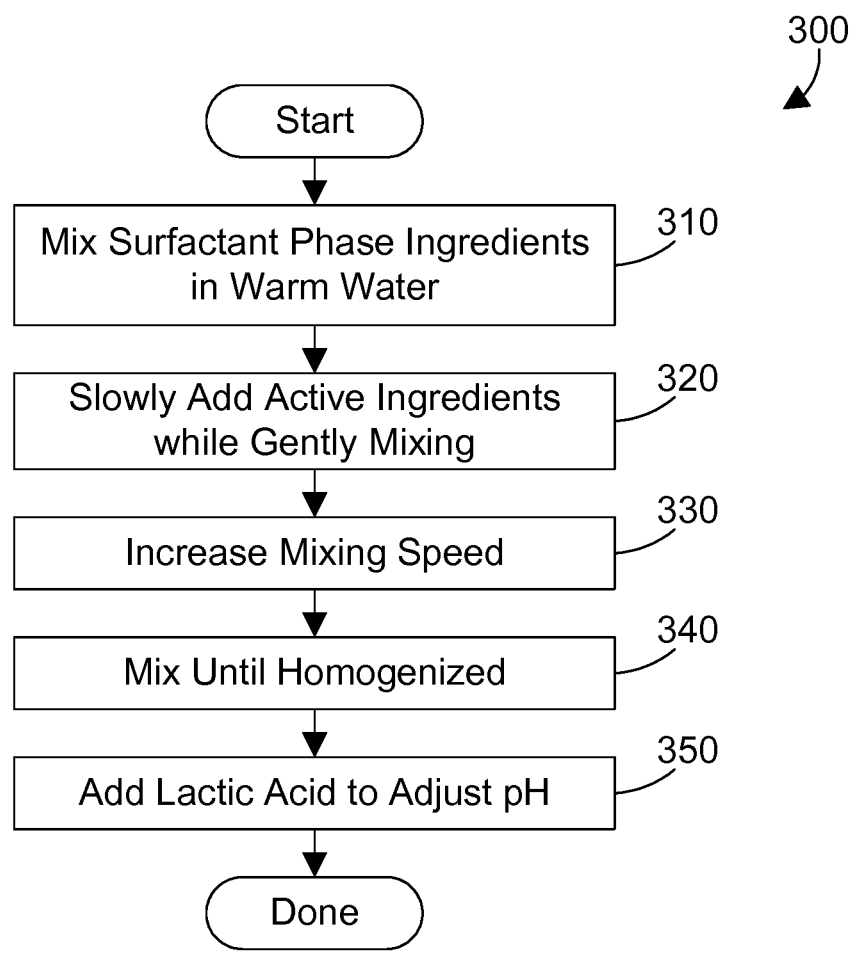
FIG. 3 is a flow diagram of a method for manufacturing a liquid soap topical sanitizer that includes avenanthramides such as a foam soap or alcohol-free sanitizing foam.

A second specific embodiment of the topical sanitizer is a foam soap that includes avenanthramides. A foam soap is one type of liquid soap. A method 300 in FIG. 3 represents a method that may be used to make foam soap. Method 300 begins by premixing the surfactant phase ingredients, specifically the PEG-80 sorbitan laurate, sodium trideceth sulfate, cocamidopropyl betaine, and PEG-150 distearate in a suitable volume of water, such as 50 grams, warmed preferably to a temperature of 35 to 45° C. (step 310). The active ingredients including the avenanthramides and vitamin E are then added slowly to the warm water while gently mixing (step 320). The mixing speed is increased to homogenize the mixture (step 330). Mixing continues until the mixture is homogenized (step 340). Lactic acid is then added to adjust the pH of the mixture (step 350). The quantity of lactic acid may vary due to variations in the other ingredients. The pH has a preferred range of 4.0 to 6.0, has a more preferred range of 4.5 to 5.5, and is most preferably approximately 5.0.

The specific ingredients and proportions for the foam soap are preferably:

| | |
|---|---|
| PEG-80 sorbitan laurate | 5-40 grams |
| Sodium trideceth sulfate | 5-40 grams |
| Cocamidopropyl betaine | 1-10 grams |
| PEG-150 distearate | >1 gram |
| Avenanthramides | determined by use profile |
| Vitamin E USP (DL-alpha tocopheryl acetate) | >0.1 grams |
| Lactic acid (90%) | q.s. |
| Deionized water | balance to make 100 gram batch |

In accordance with method 300 in FIG. 3, the PEG-80 sorbitan laurate, sodium trideceth sulfate, and cocamidopropyl betaine are premixed with a suitable quantity (such as 50 grams) of water in step 310 and gently mixed. The active ingredients including avenanthramides and vitamin E are added and mixed (step 320). The mixing speed is then increased (step 330) and the batch is mixed until homogenized (step 340). Lactic acid is then added to adjust the pH (step 350). The quantity of lactic acid varies due to variability of the other ingredients. The term "q.s." used above to indicate the amount of lactic acid is known in the art to be an abbreviation for "Quantum Sufficiat", a Latin term meaning a sufficient quantity. Once enough lactic acid has been added to achieve the desired pH, water is added to bring the batch to 100 grams total weight.

A suitable combination of these ranges will preferably sum to 100 grams, which means the numbers also express a percentage of each ingredient by weight in the foam soap. Zinc acetate could also be added to this formulation. The preferred proportion of zinc acetate is 0.1-2.0 percent by weight of the foam soap. The more preferred proportion of zinc acetate is 0.1-0.5 percent by weight of the foam soap. The most preferred proportion of zinc acetate is 0.2 percent by weight of the foam soap.

The specific ingredients and proportions for the foam soap are more preferably:

| | |
|---|---|
| PEG-80 sorbitan laurate | 10-30 grams |
| Sodium trideceth sulfate | 10-30 grams |
| Cocamidopropyl betaine | 2-15 grams |
| PEG-150 distearate | 1-10 grams |
| Avenanthramides | determined by use profile |
| Vitamin E USP (DL-alpha tocopheryl acetate) | 0.2-1.0 grams |
| Lactic acid (90%) | q.s. |
| Deionized water | balance to make 100 gram batch |

As above, zinc acetate could also be added to provide skin protectant properties for the foam soap in the ranges or specific proportion discussed above.

The specific ingredients and proportions for the foam soap are most preferably:

| | |
|---|---|
| PEG-80 sorbitan laurate | 15 grams |
| Sodium trideceth sulfate | 15 grams |
| Cocamidopropyl betaine | 3.33 grams |
| PEG-150 distearate | 1.6 grams |
| Avenanthramides | determined by use profile |
| Vitamin E USP (DL-alpha tocopheryl acetate) | 0.5 grams |
| Lactic acid (90%) | q.s. |
| Deionized water | balance to make 100 gram batch |

As above, zinc acetate could also be added to provide skin protectant properties for the foam soap in the ranges or specific proportions discussed above. For the proportions shown above, 0.20 grams of zinc acetate is added, with a corresponding reduction in the amount of water by 0.20 grams to keep the total at 100 grams so the proportions reflect percentages by weight in the foam soap.

Figure 4:
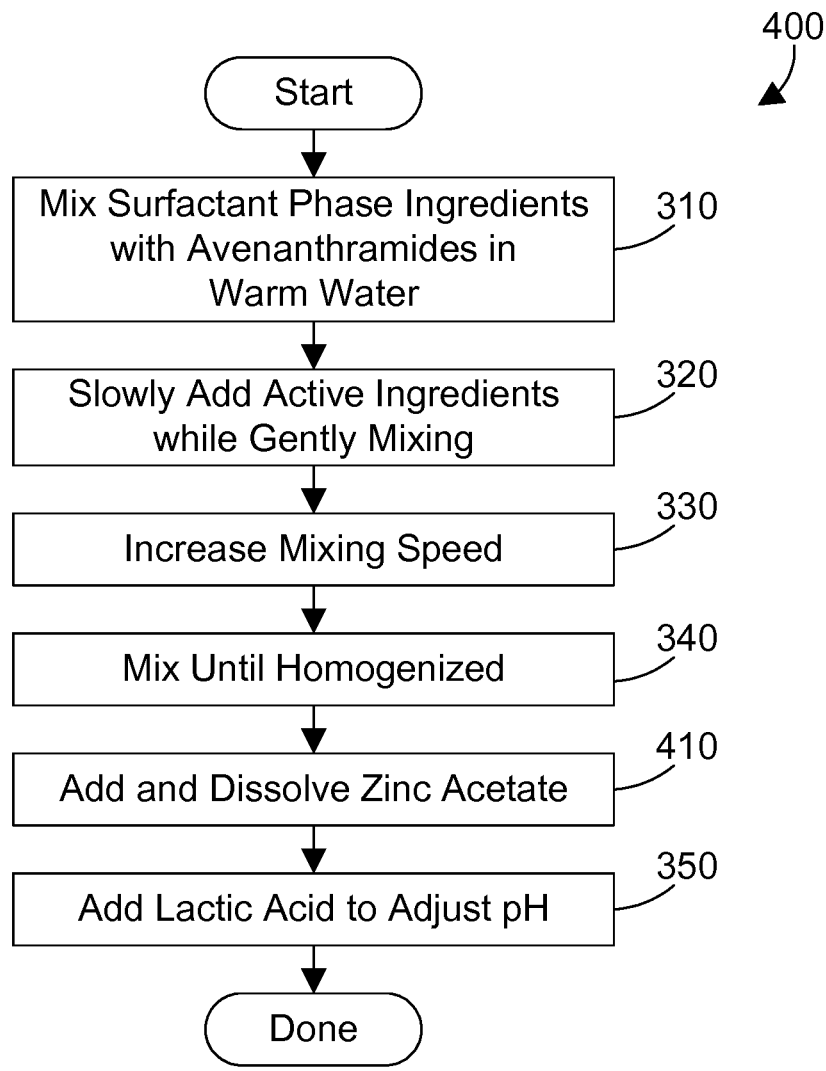
FIG. 4 is a flow diagram of a method for manufacturing a liquid soap topical sanitizer that includes avenanthramides and zinc acetate, such as a foam soap or alcohol-free sanitizing foam.

Method 400 in FIG. 4 shows one suitable method for including zinc acetate in the foam soap. The steps 310, 320, 330, 340 and 350 are the same as the steps shown in FIG. 3. The difference in FIG. 4 is the addition of the zinc acetate in step 410. Because zinc acetate is a skin protectant, adding zinc acetate to the foam soap allows the foam soap to claim skin protectant properties.

The methods shown in FIGS. 3 and 4 may also be used to manufacture an alcohol-free sanitizing foam. While the process is similar, the specific ingredients and their proportions are different. One ingredient that is added is benzalkonium chloride, which is available under the name Nobac from Mason Chemical Co., 721 West Algonquin Road, Arlington Heights, Ill. 60005. The specific ingredients and proportions for the alcohol-free sanitizing foam are preferably:

| | |
|---|---|
| PEG-80 sorbitan laurate | 0.83-6.67 grams |
| Sodium trideceth sulfate | 0.83-6.67 grams |
| Cocamidopropyl betaine | 0.16-1.67 grams |
| PEG-150 distearate | >0.16 grams |
| Avenanthramides | determined by use profile |
| Vitamin E USP (DL-alpha tocopheryl acetate) | >0.1 grams |
| Benzalkonium Chloride | 0.1-1.0 grams |
| Lactic acid (90%) | q.s. |
| Deionized water | balance to make 100 gram batch |

A suitable combination of these ranges will preferably sum to 100 grams, which means the numbers also express a percentage of each ingredient by weight in the foam soap. Zinc acetate could also be added to this formulation. The preferred proportion of zinc acetate is 0.1-2.0 percent by weight of the alcohol-free sanitizing foam. The more preferred proportion of zinc acetate is 0.1-0.5 percent by weight of the alcohol-free sanitizing foam. The most preferred proportion of zinc acetate is 0.2 percent by weight of the alcohol-free sanitizing foam.

The specific ingredients and proportions for the alcohol-free sanitizing foam are more preferably:

| | |
|---|---|
| PEG-80 sorbitan laurate | 1.67-5.0 grams |
| Sodium trideceth sulfate | 1.67-5.0 grams |
| Cocamidopropyl betaine | 0.33-2.5 grams |
| PEG-150 | 0.16-1.6 grams |
| Avenanthramides | determined by use profile |
| Vitamin E USP (DL-alpha tocopheryl acetate) | 0.2-1.0 grams |
| Benzalkonium Chloride | 0.1-0.2 grams |
| Lactic acid (90%) | q.s. |
| Deionized water | balance to make 100 gram batch |

As above, zinc acetate could also be added to provide skin protectant properties for the foam soap in the ranges or specific proportion discussed above.

The specific ingredients and proportions for the alcohol-free sanitizing foam are most preferably:

| | |
|---|---|
| PEG-80 sorbitan laurate | 2.5 grams |
| Sodium trideceth sulfate | 2.5 grams |
| Cocamidopropyl betaine | 0.55 grams |
| PEG-150 distearate | 0.27 grams |
| Avenanthramides | determined by use profile |
| Vitamin E USP (DL-alpha tocopheryl acetate) | 0.5 grams |
| Benzalkonium Chloride | 0.13 grams |
| Lactic acid (90%) | q.s. |
| Deionized water | balance to make 100 gram batch |

As stated above, zinc acetate could also be added to this alcohol-free sanitizing foam in the ranges or specific proportion discussed above. For the proportions shown above, 0.20 grams of zinc acetate is added, with a corresponding reduction in the amount of water by 0.20 grams to keep the total at 100 grams so the proportions reflect percentages by weight in the alcohol-free sanitizing foam.

The specific ingredients and proportions above can be generalized. PEG-80 sorbitan laurate is a non-ionic surfactant. Sodium trideceth sulfate is an anionic surfactant. Cocamidopropyl betaine is a zwitterionic surfactant. The foam soap and alcohol-free sanitizing foam could include any formulation that includes one or more surfactants, a concentration of avenanthramides, and may include other optional skin conditioning agents, such as glycerin, vitamin E or other emollients. To generalize even further, the disclosure and claims herein expressly extend to any topical sanitizer that includes any surfactant and a concentration of avenanthramides less than 0.01 ppm.

Figure 5:
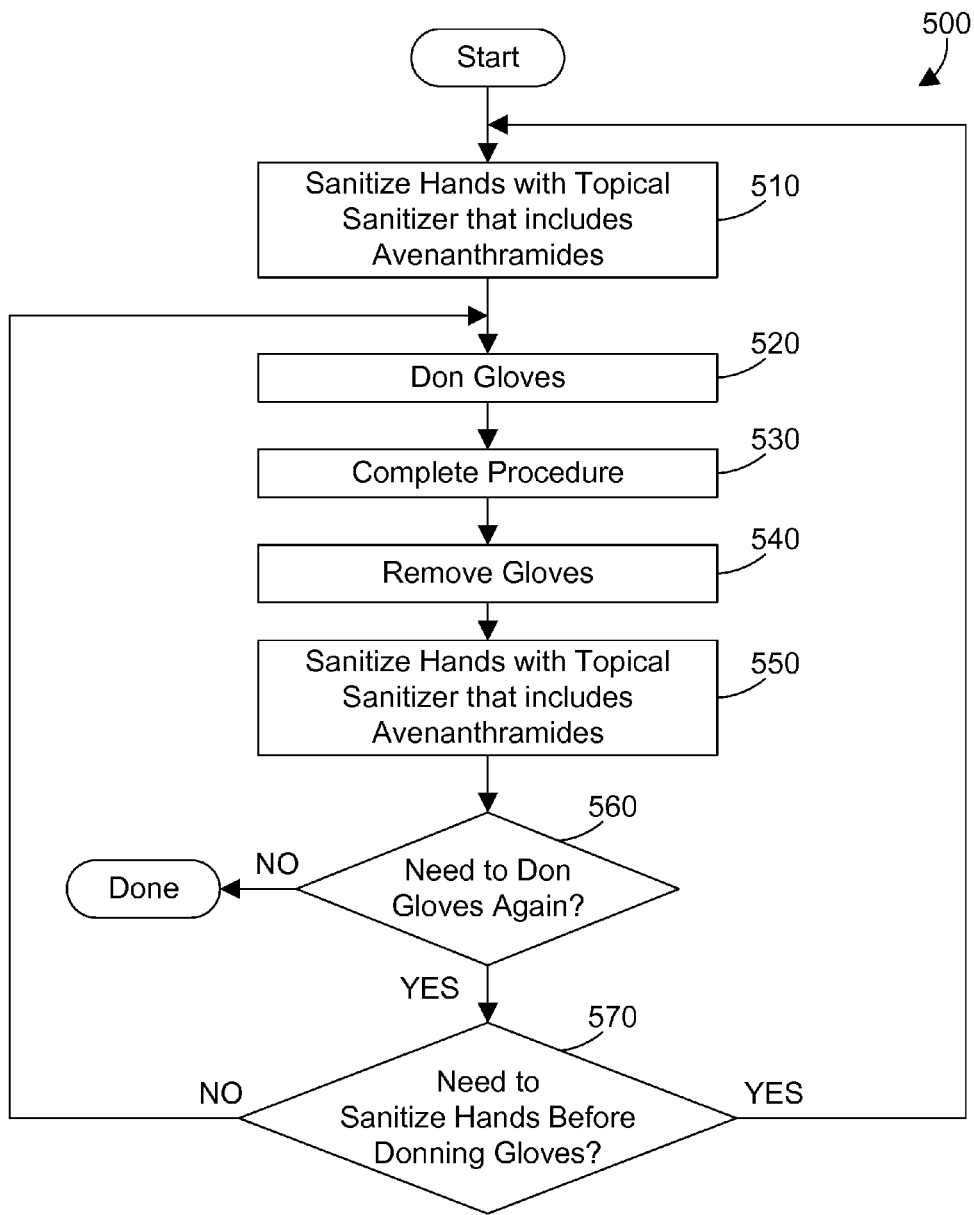
FIG. 5 is a flow diagram that illustrates how people who wear gloves at work repeatedly use one or more topical sanitizers during the workday.

Using topical sanitizers that include avenanthramides keeps a person's skin healthy and helps to heal damaged skin. Referring to FIG. 5, a method 500 for conditioning skin on hands begins when a person sanitizers his or her hands with a topical sanitizer that includes avenanthramides (step 510). The person then dons gloves (step 520). The person then completes the procedure that required the gloves (step 530), removes the gloves (step 540), and typically discards the gloves. The person may then sanitize his or her hands with a topical sanitizer that includes avenanthramides (step 550). If the person does not need to don gloves again (step 560=NO), method 500 is done. If the person needs to don gloves again (step 560=YES), a determination is made whether the person needs to sanitize his or her hands again before donning the gloves (step 570). This determination may be made according to government health mandates, according to standard practices in the industry, according to company policy, or according to instructions provided with the topical sanitizer and gloves. For example, if the person just removed gloves in step 540 and sanitized her hands in step 550 and immediately needs to don gloves again, there may be no need to sanitize the hands again before donning a new pair of gloves (step 570=NO). If there is no need to sanitize the hands again before donning a new pair of gloves (step 570=NO), method 500 loops back to step 520 and continues. If, however, the person sanitized her hands in step 550 some time ago, she may need to sanitizer her hands again before donning a new pair of gloves (step 570=YES). In this case, method 500 loops back to step 510 and continues. Note that a person could use different topical sanitizers in steps 510 and 540 according to their location and convenience. Thus, if a doctor is sanitizing her hands before examining a patient in her office, she may use the alcohol-based sanitizing gel from a bottle available in her office. If the doctor is scrubbing up for surgery, the doctor may use the foam soap. If the doctor is making rounds in a hospital, the doctor may use the alcohol-free sanitizing foam from a belt dispenser or wristband dispenser. Method 500 illustrates that regardless of how many times a person changes gloves and has to sanitize his or her hands, that person can enjoy the benefits of avenanthramides on their hands throughout the day after taking the gloves off.

The specific formulations above are given by way of example. Many variations are possible within the scope of the disclosure and claims herein, which expressly extend to any suitable formulation that includes avenanthramides and optionally includes zinc acetate.

Known compositions for treating skin that include avenanthramides typically include a relatively high concentration of avenanthramides. This is because these compositions are intended to treat the skin in a single application. U.S. Patent Application Publication No. 2008/0268077 to Vielhaber discloses a mixture that includes avenanthramides in the amount of 0.0001 to 20 wt. %, particularly preferably 0.001 to 10 wt. %, in particular 0.05 to 5 wt. %. In Vielhaber, the lowest concentration of avenanthramides of 0.0001 wt. % equates to 100 parts per million avenanthramides. U.S. Patent Application Publication No. 2007/0059390 to Magee discloses a composition that includes from about 0.05 ppm to about 100 ppm avenanthramides, for example from about 0.5 to about 50 ppm, or from about 1 ppm to about 10 ppm. In Magee, the lowest concentration of avenanthramides is 0.05 ppm. U.S. Pat. No. 6,818,232 to Redmond et al. discloses compositions that include avenanthramides in a concentration of between 0.01 and 150 ppm, more preferably between 0.01 and 50 ppm, even more preferably between 0.3 and 15 ppm, and most preferably between 1.5 and 4.5 ppm. In Redmond, the lowest concentration of avenanthramides is 0.01 ppm. Thus, 0.01 ppm avenanthramides is the lowest concentration of avenanthramides in these three references. Due to the several ranges recited in these three references, one must conclude that having a concentration of avenanthramides less than 0.01 ppm would be ineffective in the compositions disclosed in Vielhaber, Magee and Redmond discussed above.

The preferred embodiments herein allow using a concentration of avenanthramides less than 0.01 ppm while still providing benefit to the skin. This is because many people, especially healthcare workers, change gloves dozens of times each day, and typically sanitize their hands both before donning gloves and after removing gloves. An effective amount of avenanthramides can be delivered to the skin using sanitizer compositions that include less than 0.01 ppm avenanthramides due to the repeated application of sanitizer during the workday. Introduced herein is the concept of a "use profile", which means a number of applications of one or more sanitizers over a specified time period. One example of a suitable time period is the length of a work shift for a healthcare worker. By taking into account the number of applications of one or more sanitizers during a specified time period, sanitizers with concentrations of avenanthramides less than 0.01 ppm may be used. Examples follow to illustrate.

Figure 6:
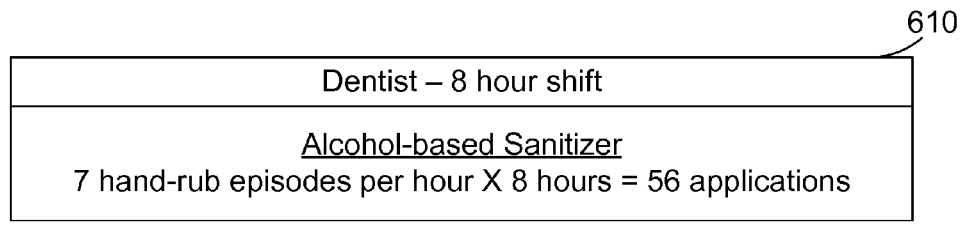
FIG. 6 is a sample use profile for a dentist that uses an alcohol-based sanitizer.

Referring to FIG. 6, a sample use profile 610 for a dentist working an 8 hour shift shows an average of seven hand-rub episodes with an alcohol-based sanitizer per hour for eight hours, resulting in 56 applications per shift. An appropriate concentration of avenanthramides for the sanitizer may then be determined using method 700 in FIG. 7. Method 700 begins by determining a use profile that includes a number of applications of the sanitizer over a specified time period, such as a work shift (step 710). Use profile 610 is one suitable example of a use profile determined in step 710. A target amount of avenanthramides for the specified time period is then determined (step 720). The target amount of avenanthramides is then divided by the number of applications in the use profile to determine a desired exposure of avenanthramides per application (step 730). A topical sanitizer that includes a concentration of avenanthramides that provides at least the desired exposure of avenanthramides per application is provided (step 740). Note that because of the repeated application of sanitizers, the concentration of avenanthramides can be less that taught in the prior art, and in some cases orders of magnitude less.

Figure 8:
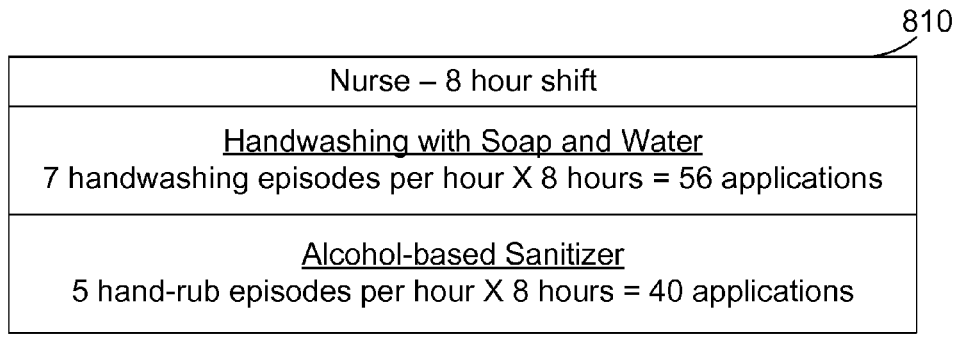
FIG. 8 is a sample use profile for a nurse.

FIG. 8 shows a sample use profile 810 for a nurse working an eight hour shift that includes 56 applications with soap and water, and 40 applications of an alcohol-based sanitizer. Appropriate concentrations of avenanthramides for the two sanitizers may then be determined using method 900 in FIG. 9. Method 900 begins by determining the use profile that includes a number of applications of first and second sanitizers over a specified time period (step 910). Use profile 810 is one suitable example of a use profile determined in step 910. A target amount of avenanthramides for the specified time period is then determined (step 920). The first concentration of avenanthramides of the first sanitizer and the second concentration of avenanthramides for the second sanitizer are then determined to provide at least the target amount of avenanthramides in the specified time period (step 930). A first sanitizer is then provided with a minimum of the first concentration of avenanthramides (step 940) and a second sanitizer is provided with a minimum of the second concentration of avenanthramides (step 950). Again, because of the repeated application of sanitizers, the concentration of avenanthramides can be less that taught in the prior art, and in some cases orders of magnitude less.

Figure 7:
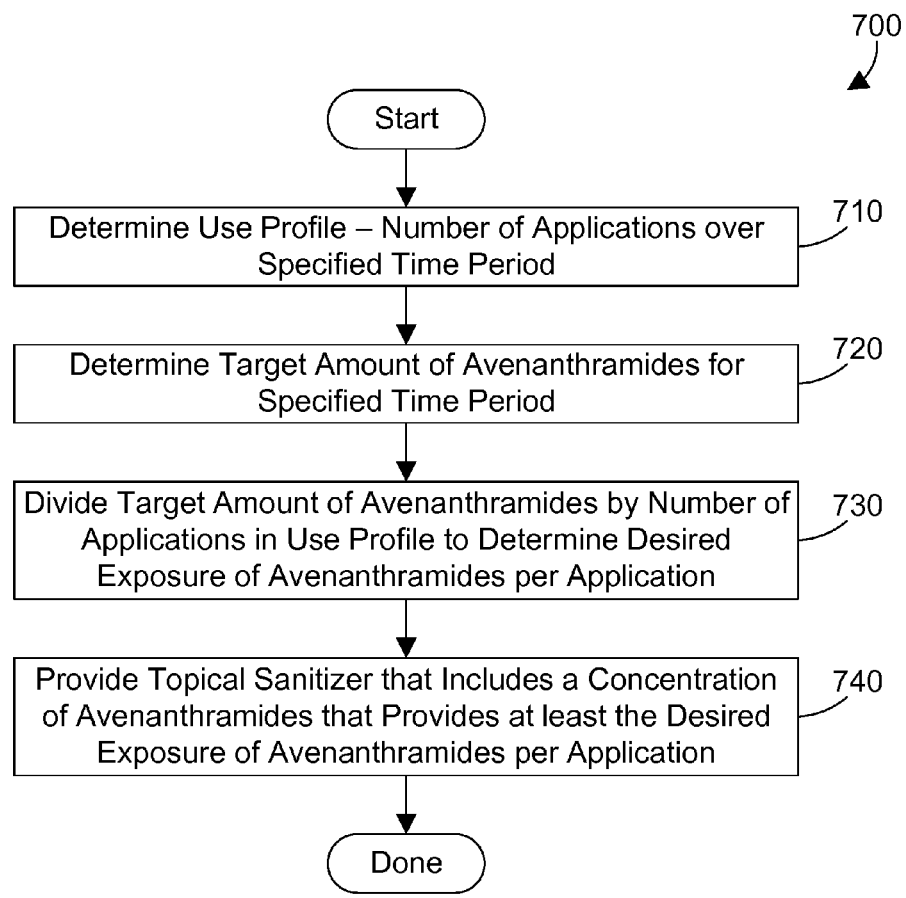
FIG. 7 is a flow diagram of a method for determining a desired minimum concentration of avenanthramides based on a use profile.
Figure 9:
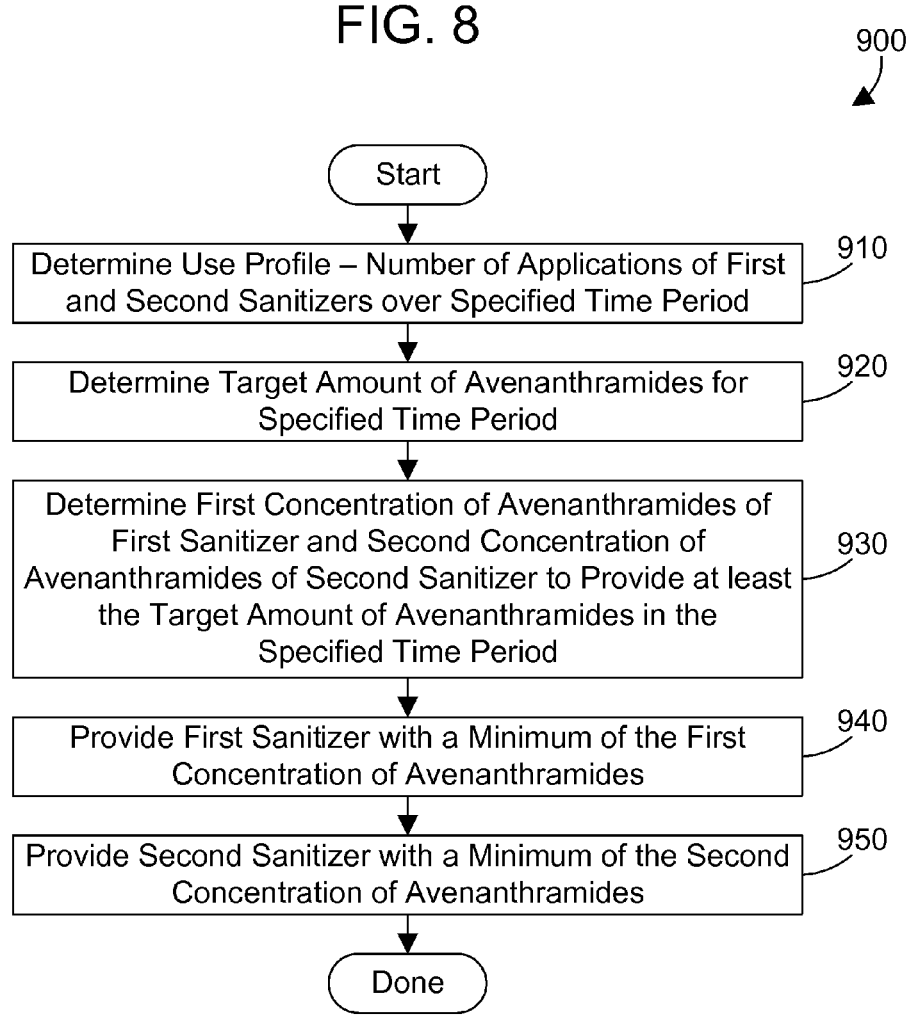
FIG. 9 is a flow diagram of a method for providing two sanitizers with concentrations of avenanthramides determined from the target amount of avenanthramides for a specified time period and a use profile.

The example shown in FIGS. 6 and 7 is for determining concentration of avenanthramides in a single sanitizer. The example shown in FIGS. 8 and 9 is for determining concentration of avenanthramides in two sanitizers. Note that other use profiles could include more than two sanitizers within the scope of the disclosure and claims herein.

Many compositions for treating skin that include avenanthramides are formulated with a relatively high concentration of avenanthramides for the purpose of repairing or relieving damaged skin. In the case of a person who uses sanitizer dozens of time a day, there is no need for such a high concentration of avenanthramides, especially if the skin is not damaged. FIG. 10 shows two different target amounts of avenanthramides, 0.1 microgram per day for maintaining healthy skin, and 1.0 microgram per day to repair or relieve damaged skin. Using these target amounts and the use profiles in FIGS. 6 and 8, we can now determine minimum concentrations of avenanthramides for sanitizers that satisfy the use profile and the target amount of avenanthramides.

Referring to FIG. 11, for the dentist with the use profile 610 in FIG. 6 who has 56 applications per day of a single sanitizer, skin maintenance can be performed with a minimum concentration of 0.001 ppm avenanthramides, which is an order of magnitude lower than the 0.01 ppm lower bound of avenanthramides in the Redmond patent referenced above. Note this assumes use of 1.8 ml sanitizer in each application. For repair or relief of damaged skin, a minimum concentration of 0.01 ppm avenanthramides can be used.

FIG. 12 shows minimum concentration of avenanthramides for the nurse with the use profile 810 in FIG. 8. Skin maintenance can be performed with two sanitizers that have an average minimum concentration of 0.00058 ppm avenanthramides. Note this also assumes use of 1.8 ml sanitizer in each application. For repair or relief of damaged skin, a minimum concentration of 0.0058 ppm avenanthramides can be used. Both of these minimum concentrations of avenanthramides in FIG. 12 are significantly less than the 0.01 ppm lower bound of avenanthramides in the Redmond patent referenced above.

FIG. 13 shows one specific example of how the concentrations of multiple sanitizers may be determined. In this example, we assume that first a minimum concentration of the alcohol-based sanitizer is determined to be 0.001 ppm avenanthramides. With that known minimum concentration of avenanthramides for the alcohol-based sanitizer, and the target amount of avenanthramides, we can then calculate the minimum concentration of avenanthramides for the soap. As shown in FIG. 13, for a target amount of avenanthramides of 0.1 micrograms per day, and the minimum concentration of 0.001 ppm avenanthramides in the alcohol-based sanitizer, the minimum concentration of avenanthramides in the soap is 0.00028 ppm. Similarly, for a target amount of avenanthramides of 1.0 micrograms per day, and the minimum concentration of 0.001 ppm avenanthramides in the alcohol-based sanitizer, the minimum concentration of avenanthramides in the soap is 0.00921 ppm. This example shows that minimum concentrations of two or more sanitizers can be computed based on the target amount of avenanthramides per day and based on the use profile. While the specific example in FIG. 13 first sets a minimum concentration of avenanthramides for the alcohol-based sanitizer, then computes the minimum concentration of avenanthramides for the soap, one skilled in the art will understand that both could be computed based on mathematical formulae. The disclosure and claims herein extend to determining the minimum concentration of avenanthramides in any suitable number of sanitizers using any suitable methodology based on the use profile that specifies number of applications of each sanitizer in a specified time period and based on the target amount of avenanthramides.

Note the minimum concentrations of avenanthramides shown in FIGS. 11-13 are just that, minimums. This does not mean that a sanitizer needs to be manufactured with the exact minimum concentrations shown. Rather, these calculations are meant as a guide to selecting a sanitizer with a concentration of avenanthramides that satisfies the minimum concentrations. Thus, for the example in FIG. 13, using an alcohol-based sanitizer that has a concentration of 0.001 ppm avenanthramides and using a soap that has a concentration of 0.001 ppm avenanthramides will provide more that the specified minimum of 0.1 micrograms per day of avenanthramides.

In the specific examples in FIG. 13, the concentration of avenanthramides for both the alcohol-based sanitizer and the soap is less than 0.01 ppm avenanthramides. In other examples, one sanitizer might have a minimum concentration of avenanthramides greater than 0.01 ppm while another has a minimum concentration of avenanthramides less than 0.01 ppm. The disclosure and claims herein extend to any suitable sanitizer of combination of sanitizers where at least one of the sanitizers has a concentration of avenanthramides less than 0.01 ppm.

By taking the use profile into account, which specifies repeated and frequent application of sanitizer throughout a worker's shift, the minimum concentration of avenanthramides may be determined. Thus, as shown for the target amount of 0.1 micrograms/day of avenanthramides, an alcohol-based sanitizer that has a concentration of 0.001 ppm avenanthramides and a soap that has a concentration of 0.0005 ppm would satisfy the use profile and the target amount of avenanthramides. Note these concentrations of avenanthramides are orders of magnitude less than what the prior art believed would be an effective dose of avenanthramides. This is because of the cumulative effect of using the sanitizer dozens of times each day, which has a cumulative beneficial effect on the skin due to the avenanthramides penetrating the skin with each use. The benefit of having concentrations of avenanthramides substantially less that prior art compositions is reduced cost. Adding avenanthramides to a composition increases its cost. To the extend the amount of avenanthramides can be reduced, the resulting cost of the compositions is also reduced. The sanitizers disclosed and claimed herein thus provide a competitive advantage by providing lower-cost sanitizers that include avenanthramides.

While specific minimum concentrations of avenanthramides are shown in the examples herein for the purpose of illustration, any suitable concentration of avenanthramides in a sanitizer may be effective to treat skin based on the use profile. In addition, future research may prove beneficial effects from much lower concentrations of avenanthramides that was previously thought possible. The disclosure and claims herein expressly extends to any suitable concentration of avenanthramides, including many orders of magnitude smaller than the minimum concentrations of avenanthramides disclosed in the examples herein.

The topical sanitizers disclosed herein provide significant advantages over currently-known methods discussed above. By allowing avenanthramides to be in contact with a person's skin each time a person sanitizes his or her hands, the skin on the person's hands will be softer and any skin irritation will be greatly reduced. The result is much greater comfort to the hands. The skin will be softer and smoother when in good health. Softer and smoother comes from the retention of oils and the maintenance of the skin barrier to prevent moisture loss, which maintains hydration. The skin is smoother because the skin cells are intact and not flaking, as well there are minimum fissures in the skin. Skin will be a normal color and not red because of the anti-irritant, anti-histamine, anti-inflammatory effect of the avenanthramides.

The specific use profiles and methods shown herein use the number of applications over a specified time period to determine a minimum concentration of avenanthramides in a sanitizer. Other methods could also be used. For example, a suitable concentration of avenanthramides for a hand sanitizer could be determined based on the time a sanitizer is in contact with the person's skin. Thus, for the use profile 810 shown in FIG. 8, if the hand washing with soap and water results in 20 seconds of exposure to the avenanthramides and the sanitizing with alcohol-based sanitizer results in 15 seconds of exposure to the avenanthramides, the total time of exposure to avenanthramides will be 56×20 seconds+40×15 seconds=1,720 seconds of exposure to avenanthramides per 8 hour shift. A concentration of avenanthramides could then be determined to provide the desired minimum exposure to avenanthramides, which could be expressed in new units such as "parts-per-million minutes" based on the use profile that specifies time of exposure to avenanthramides.

The avenanthramides could be encapsulated nanosomes/oleosomes/liposomes. These are delivery vehicles used to enhance delivery of avenanthramides to the epidermis and dermis. These compositions are typically oil in water suspensions or water in oil suspensions that may have avenanthramides encapsulated or incorporated into their structure. The methods of manufacturing are known to those skilled in the art. The compositions may also incorporate other ingredients, for example, vitamin E to further enhance the skin conditioning benefits of the avenanthramides. The water phase may also include alcohol or surfactants. Known methods for making liposomes and liposome compositions are disclosed in U.S. Patent Application Publication No. 2012/0171280 to Zhang.

The specification and claims herein support a topical sanitizer comprising: alcohol; and a concentration of avenanthramides of less than 0.01 parts per million.

The specification and claims herein further support a topical sanitizer comprising: at least one surfactant; and a concentration of avenanthramides of less than 0.01 parts per million.

The specification and claims herein additionally support a skin treatment system comprising: a topical sanitizer that comprises a concentration of avenanthramides; a use profile for a user that comprises number of applications of the topical sanitizer over a specified time period; and wherein the concentration of avenanthramides is determined based on the use profile for the user.

The specification and claims herein further support a skin treatment system comprising: a first sanitizer that comprises a first concentration of avenanthramides; a second sanitizer that comprises a second concentration of avenanthramides; a use profile for a user that comprises number of applications of the first sanitizer and number of applications of the second sanitizer over a specified time period; and wherein the first concentration of avenanthramides and the second concentration of avenanthramides are determined based on the use profile for the user.

Topical sanitizers including alcohol-based gels, alcohol-based foams, alcohol-free foams, liquid soaps, alcohol-based wipes, and alcohol-based sprays include avenanthramides, which is an active component of oats that is beneficial to the skin. The concentration of avenanthramides can be substantially less when considering the use profile of the person using the sanitizers. Many healthcare workers sanitize their hands dozens of times a day. An effective dose of avenanthramides can be delivered to the skin even when the concentration in avenanthramides is relatively low due to the repeated application of the sanitizers during the day. In addition, a lower concentration of avenanthramides may be used to maintain healthy skin compared to a higher concentration that may be used to repair damaged skin. Minimum concentrations of avenanthramides in one or more topical sanitizers can be determined according to the use profile and the target amount of avenanthramides to deliver via the topical sanitizers.

One skilled in the art will appreciate that many variations are possible within the scope of the claims. Thus, while the disclosure is particularly shown and described above, it will be understood by those skilled in the art that these and other changes in form and details may be made therein without departing from the spirit and scope of the claims.

The invention claimed is:

1. A method for manufacturing a plurality of sanitizers comprising:
   determining a use profile that comprises a first number of applications of a first sanitizer to skin over a specified time period and a second number of applications of a second sanitizer to the skin over the specified time period;
   determining a target amount of avenanthramides for treating the skin for the specified time period;
   determining a first concentration of avenanthramides for the first sanitizer and a second concentration of avenanthramides for the second sanitizer to provide at least the target amount of avenanthramides for the specified time period based on the use profile;
   mixing a first plurality of ingredients to provide the first sanitizer that includes the first concentration of avenanthramides; and
   mixing a second plurality of ingredients to provide the second sanitizer that includes the second concentration of avenanthramides.

2. The method of claim 1 wherein the first and second concentrations of avenanthramides are different.

3. The method of claim 1 wherein the first sanitizer comprises an alcohol-based sanitizer and the second sanitizer comprises a liquid soap.

4. The method of claim 1 wherein the first sanitizer comprises an alcohol-based sanitizer and the second sanitizer comprises an alcohol-free sanitizing foam.

5. The method of claim 1 wherein the first sanitizer comprises a liquid soap and the second sanitizer comprises an alcohol-free sanitizing foam.

6. The method of claim 1 wherein the specified time period comprises length of a work shift of a healthcare worker for which the use profile is determined.

7. The method of claim 1 wherein the first concentration of avenanthramides is less than 0.01 parts per million.

8. The method of claim 1 wherein the second concentration of avenanthramides is less than 0.01 parts per million.

9. The method of claim 1 wherein the first and second sanitizers are selected from the group: alcohol-based sanitizing gel, alcohol-based sanitizing foam, liquid soap, alcohol-free sanitizing foam, alcohol-based wipes, and alcohol-based spray.

10. The method of claim 1 wherein the target amount of avenanthramides comprises at least 0.1 microgram and the specified time period comprises one day.

11. The method of claim 1 wherein the target amount of avenanthramides comprises at least 1.0 microgram and the specified time period comprises one day.

* * * * *